(12) United States Patent
Dorsey et al.

(10) Patent No.: US 11,071,481 B2
(45) Date of Patent: Jul. 27, 2021

(54) APPARATUS AND METHOD FOR DETERMINING PHYSIOLOGICAL PARAMETERS OF AN INFANT IN-UTERO

(71) Applicant: Prenatal-Hope, Inc., Seminole, FL (US)

(72) Inventors: Tammy Dorsey, Valley Center, KS (US); James Robert Balman, Wichita, KS (US)

(73) Assignee: Prenatal-Hope, Inc., Seminole, FL (US)

(*) Notice: Subject to any disclaimer, the term of this patent is extended or adjusted under 35 U.S.C. 154(b) by 7 days.

(21) Appl. No.: 16/749,794

(22) Filed: Jan. 22, 2020

(65) Prior Publication Data

US 2020/0155043 A1     May 21, 2020

Related U.S. Application Data

(63) Continuation of application No. PCT/US2019/020384, filed on Mar. 1, 2019.

(60) Provisional application No. 62/789,398, filed on Jan. 7, 2019, provisional application No. 62/663,371, filed on Apr. 27, 2018.

(51) Int. Cl.
    *A61B 5/1464*      (2006.01)
    *A61B 5/024*      (2006.01)
    *A61B 5/145*      (2006.01)

(52) U.S. Cl.
    CPC ........ *A61B 5/1464* (2013.01); *A61B 5/02411* (2013.01); *A61B 5/14539* (2013.01)

(58) Field of Classification Search
None
See application file for complete search history.

(56) References Cited

U.S. PATENT DOCUMENTS

| 4,041,932 A | 8/1977 | Fostick |
| 5,228,440 A | 7/1993 | Chung et al. |
| (Continued) | | |

FOREIGN PATENT DOCUMENTS

| WO | 95/03738 A1 | 2/1995 |
| WO | 02/100259 A1 | 12/2002 |
| WO | 2009/142599 A1 | 11/2009 |

OTHER PUBLICATIONS

Patent Cooperation Treaty, International Search Report and Written Opinion of the International Searching Authority for International Application No. PCT/US2019/020384 dated May 23, 2019, 15 pages.

*Primary Examiner* — Michael R Bloch
(74) *Attorney, Agent, or Firm* — Dykema Gossett PLLC

(57) ABSTRACT

Described herein is an apparatus to detect fetal acidosis during labor. This apparatus, which is noninvasive to the fetus, has a pH sensor and at least one fetal tissue detector. When the apparatus is inserted into the vaginal canal of a patient during labor, the pH reading determined by the pH sensor correlates to the pH of the fetus's blood. The fetal tissue detector may be a pulse oximeter, which may allow for a user to obtain the pulse rate reading of a surface contacted by the pH sensor. This pulse rate reading may be compared to an external reading of a pulse rate of the patient to confirm whether the pH sensor is contacting the fetus. During travel through the vaginal canal, the pH sensor may be protected by a protective sheath with an area of weakness to allow exposure of the pH sensor when the fetus is reached.

18 Claims, 9 Drawing Sheets

(56) References Cited

U.S. PATENT DOCUMENTS

| | | | |
|---|---|---|---|
| 5,551,424 | A | 9/1996 | Morrison et al. |
| 5,776,058 | A | 7/1998 | Levinson et al. |
| 6,058,321 | A | 5/2000 | Swayze et al. |
| 6,104,941 | A | 8/2000 | Huey et al. |
| 6,689,056 | B1 | 2/2004 | Kilcoyne et al. |
| 8,634,891 | B2 | 1/2014 | Klomhaus |
| 2006/0258909 | A1* | 11/2006 | Saadat ............... A61B 46/10 600/121 |
| 2008/0221420 | A1* | 9/2008 | Grubac ............... A61B 5/0448 600/338 |
| 2009/0076348 | A1* | 3/2009 | Manicka ............. A61B 5/053 600/301 |
| 2011/0190579 | A1* | 8/2011 | Ziarno ................ A61B 1/303 600/109 |
| 2015/0164395 | A1* | 6/2015 | McIntosh .......... G01N 27/4165 600/361 |
| 2016/0310049 | A1* | 10/2016 | Rowe ................. A61B 5/1477 |
| 2017/0000407 | A1* | 1/2017 | Saxby ................ A61B 5/1032 |
| 2017/0065298 | A1 | 3/2017 | Harris et al. |

\* cited by examiner

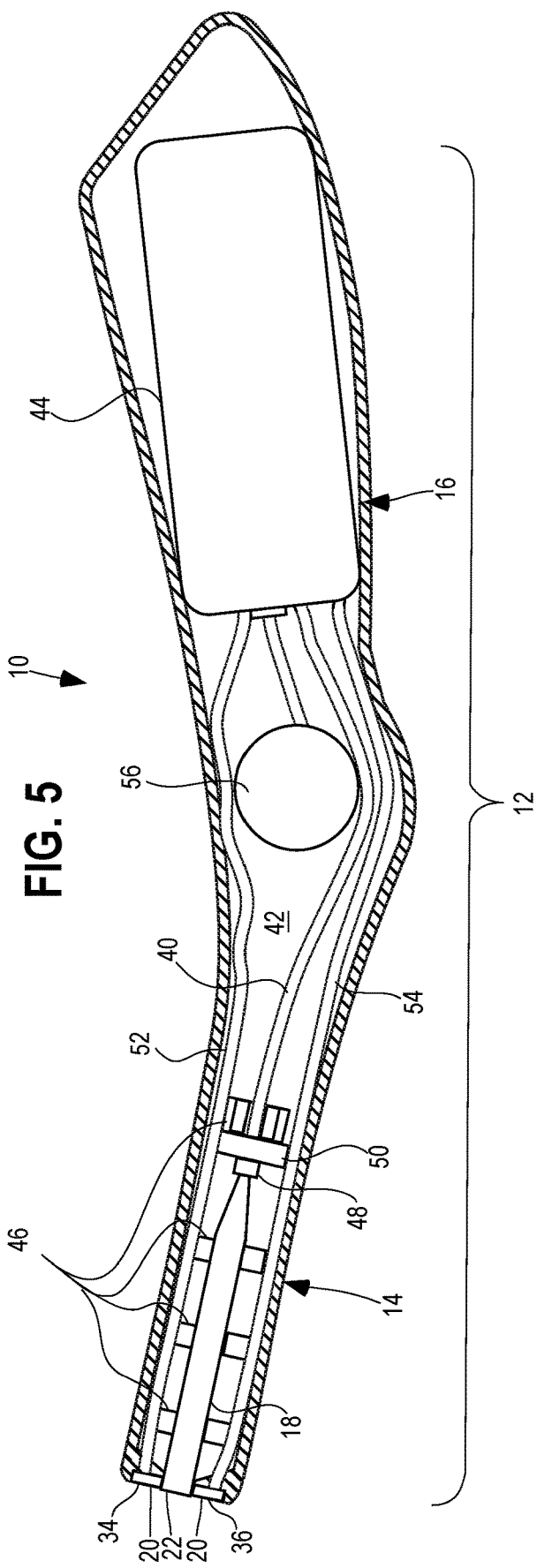

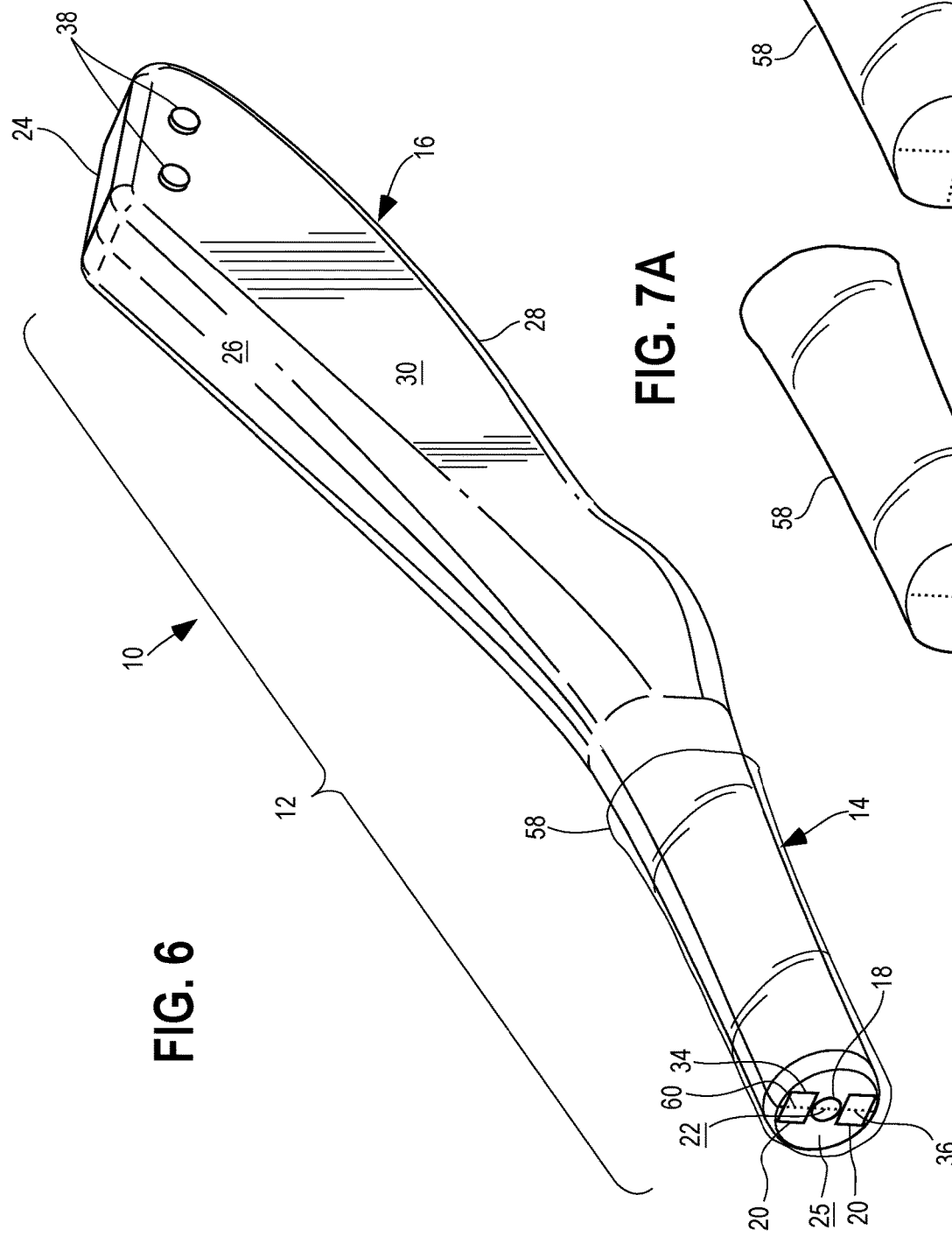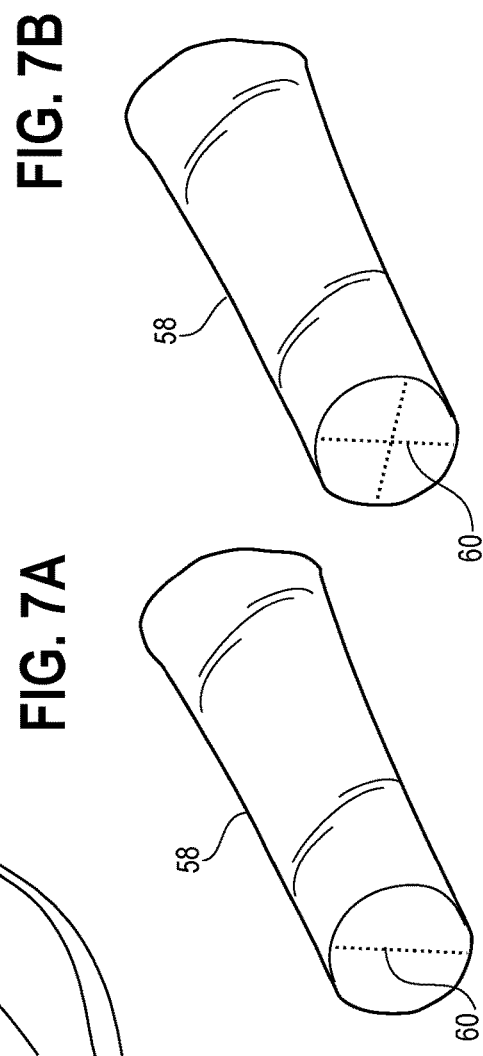

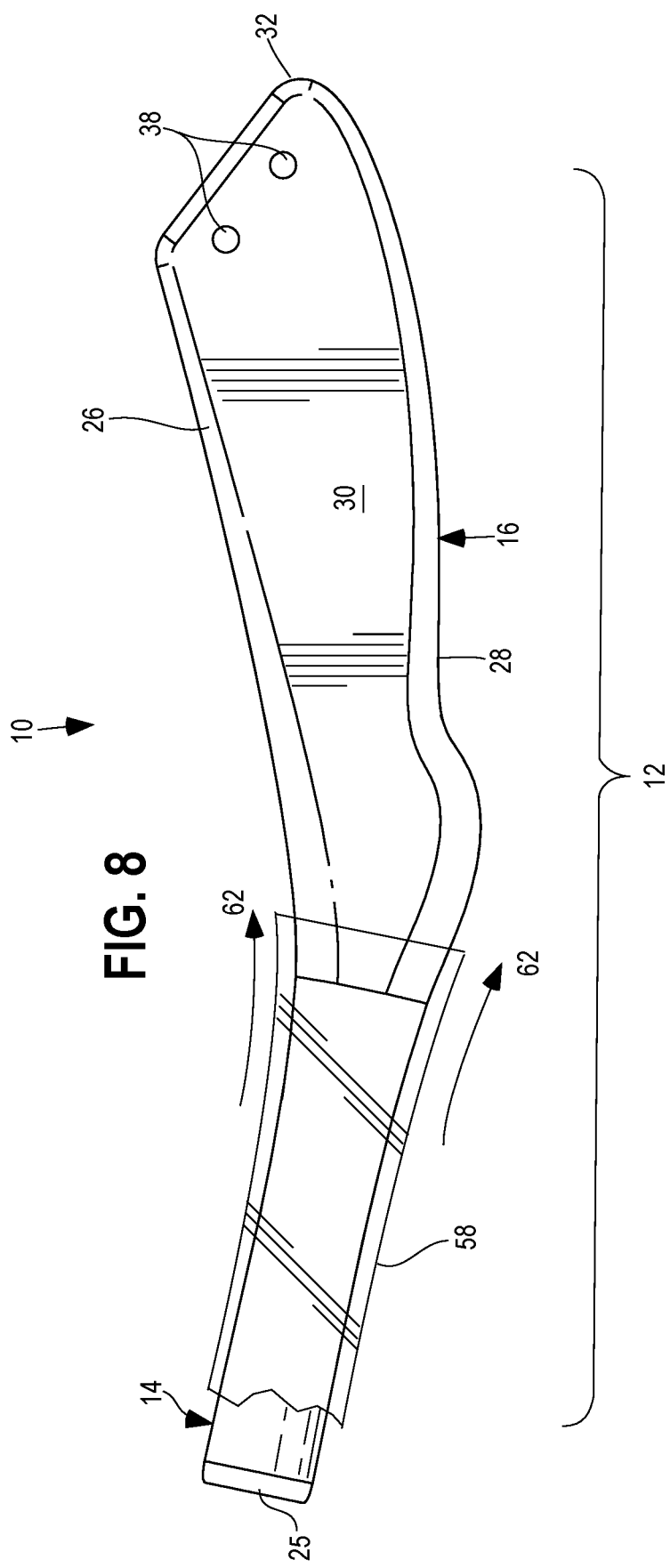

APPARATUS AND METHOD FOR DETERMINING PHYSIOLOGICAL PARAMETERS OF AN INFANT IN-UTERO

CROSS-REFERENCE TO RELATED APPLICATIONS

This application is a continuation of prior International Application Number PCT/US2019/020384, filed Mar. 1, 2019, which claims the benefit of U.S. Provisional Application No. 62/663,371, filed on Apr. 27, 2018 and U.S. Provisional Application No. 62/789,398, filed on Jan. 7, 2019.

TECHNICAL FIELD

This application relates generally to medical instruments, and more specifically, to an apparatus, which is noninvasive to a fetus, for detecting fetal acidosis in-utero and method of use thereof.

BACKGROUND

Fetal acidosis is a high level of acid in the blood of a fetus resulting from a limited oxygen supply available to the fetus over an extended period of time. Known tests for fetal acidosis, such as Doppler Ultrasonography, fetal heart rate monitoring, physical examination, and fetal blood tests are invasive or have unacceptable margins of error. For example, cordocentesis, an ultrasound-guided procedure to collect fetal blood from the umbilical cord, may not be used for routine or repeated monitoring due to its procedure-related risk. Additionally, fetal scalp sampling, an operation where the fetus's head is pierced to obtain the level of pH in the tissue, is another invasive, unreliable procedure used to attempt to diagnose fetal acidosis.

A need exists for a procedure that is less invasive to the fetus but which allows medical professionals to reliably determine whether a fetus is experiencing fetal acidosis while a patient is in labor.

SUMMARY

Described herein is an apparatus to detect fetal acidosis during labor, where use of such device is noninvasive to the fetus. The apparatus has a pH sensor and a fetal tissue detector to detect when the apparatus contacts a fetus when the apparatus is inserted into the vaginal canal of a patient.

From the pH sensor's contact with the fetus and a subsequent pH reading which may correlate to the pH of the fetus's blood, the user may reliably determine whether a fetus is experiencing fetal acidosis and take appropriate countermeasures. Other physiological parameters which may also help support a diagnosis fetal acidosis in-utero are pulse rate of the fetus and/or an oxygen saturation level of the fetus's blood.

In accordance with one aspect of the present disclosure, an apparatus is provided that detects fetal acidosis of a fetus in a patient during labor. The apparatus may include an elongated body with a first end portion and a second end portion. The first end portion may include a pH sensor with an exposed end. The first end portion may also include a fetal tissue detector. The second end portion may be grasped by a user to operate the apparatus.

The apparatus may also include a pressure sensor. In some embodiments. The pressure sensor may be a pressure switch. The apparatus may also include an optical sensor. In one form, the optical sensor may be a pulse oximeter, which may allow for a user to obtain the pulse rate reading of a surface that is contacted with the pH sensor. This pulse rate reading of the surface contacted may be compared to an external reading of a pulse rate of the patient to confirm whether the pH sensor is contacting the fetus or the patient. If the pulse rates are similar, the pH sensor is contacting the patient. If the pulse rates are dissimilar, then the pH sensor is contacting the fetus.

In some forms, the apparatus may further include a microprocessor which may be operatively coupled to the pH sensor determine a pH reading. In some embodiments, the pressure sensor and optical sensor may both be operatively coupled to the microprocessor. According to one form, a display may be operatively coupled to the microprocessor.

Some embodiments of the apparatus include a protective sheath to protect the pH sensor from early detection and/or contamination during insertion into and travel through the vaginal canal. The protective sheath may have an area of weakness. Upon force by the user, the area of weakness may be disrupted to the expose the pH sensor to the fetus to obtain the pH reading of the fetus's skin.

Rather than using a protective sheath, some embodiments include at least one flap and an annular receptacle to protect the pH sensor. The user may activate a mechanism to open and close the at least one flap, which may respectively expose and protect the pH sensor.

In one form of the present disclosure, the apparatus may include a sensor to detect a physiological parameter of a fetus. The apparatus may include an elongated body with a first end portion on an opposite end from a second end portion. The first end portion may include a sensor receiver which is operatively coupled to a sensor. A microprocessor may be operatively coupled to the sensor. A display may be operatively coupled to the sensor to show the results of the physiological parameter measured to help determine whether the fetus is experiencing fetal acidosis.

In one method of employing the apparatus with an elongated body with a pH sensor in a first end portion, a fetal tissue detector in the first end portion, and a display operatively coupled to the pH sensor and the fetal tissue detector, the first end portion of the apparatus may be inserted into a patient's vaginal canal by a user. Next, the user may determine whether the pH sensor is contacting a fetus via the fetal tissue detector. The pH sensor may then maintain contact with the fetus to transmit a pH reading. The apparatus may then be removed from the vaginal canal.

BRIEF DESCRIPTION OF THE DRAWINGS

FIG. 5 is a cross-sectional side view of the apparatus of FIG. 1;

FIG. 6 is a perspective view of the apparatus of FIG. 1 with a protective sheath surrounding at least the pH sensor;

FIG. 7A is perspective view of the protective sheath with one form of an area of weakness;

FIG. 7B is a perspective view of the protective sheath with another form of an area of weakness;

FIG. 8 is an enlarged view of a first end portion of the apparatus of FIG. 1 showing the disruption of the protective sheath to expose at least the pH sensor;

DETAILED DESCRIPTION

Figure 1:
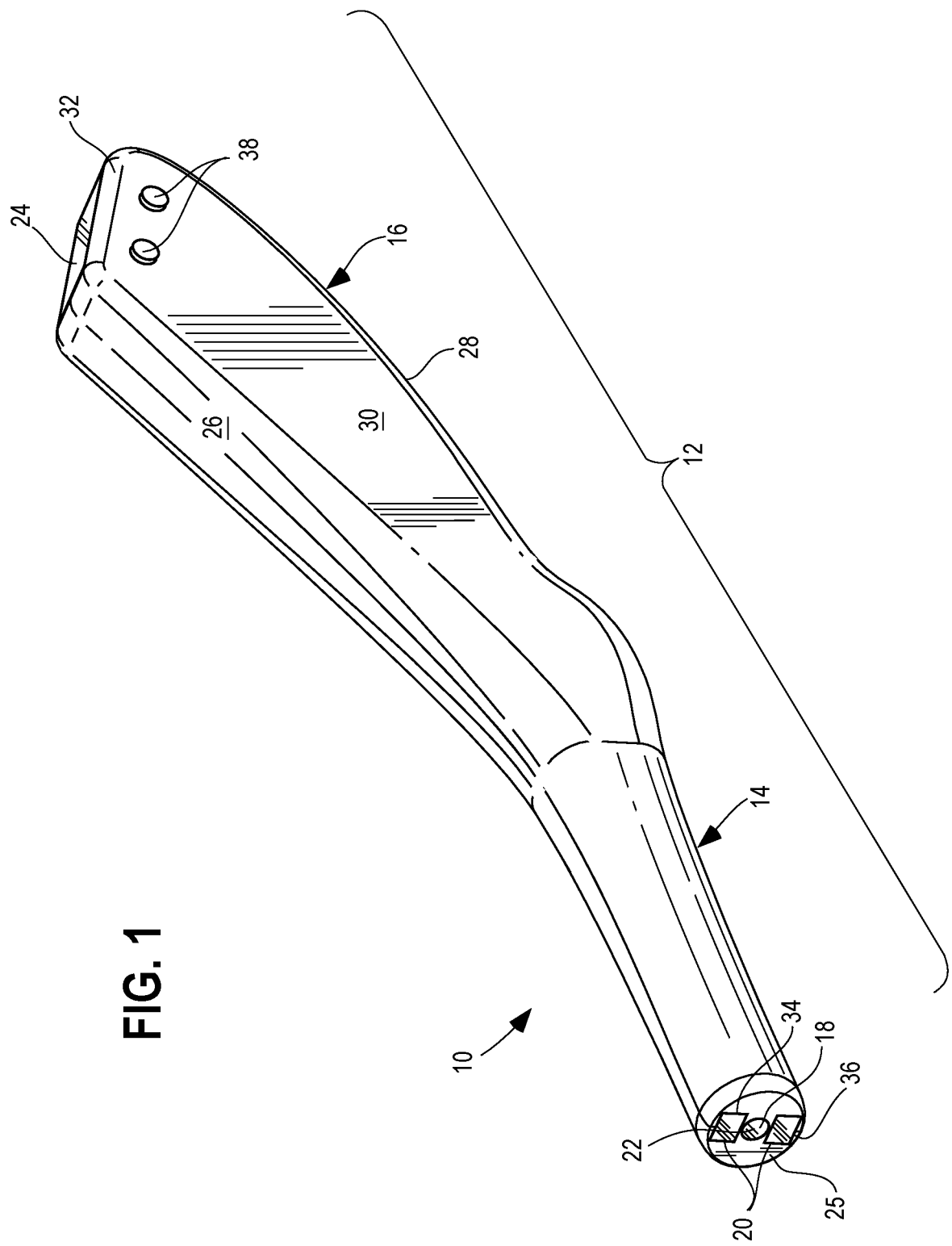
FIG. 1 is a perspective view of one form of a fetal acidosis detection apparatus.
Figure 2:
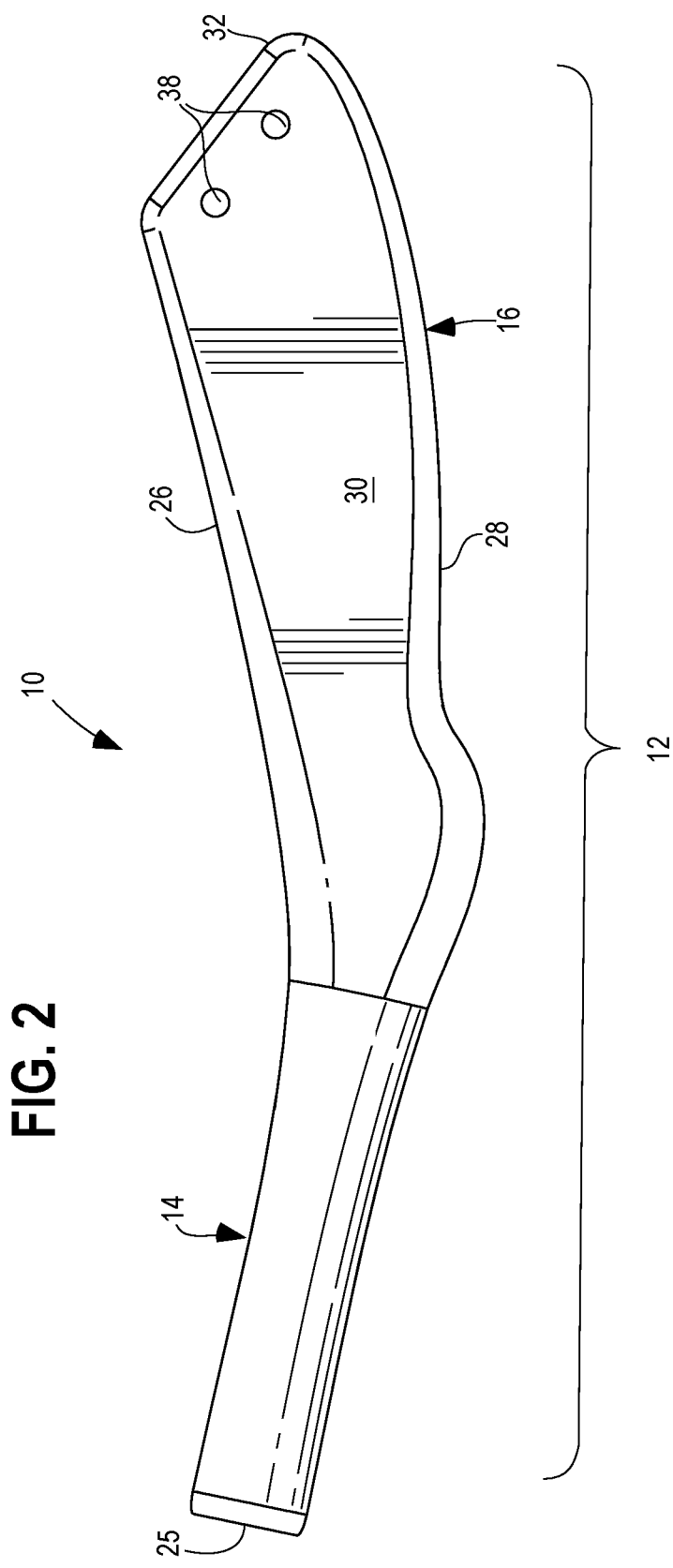
FIG. 2 is a side view of the apparatus of FIG. 1.
Figure 3:
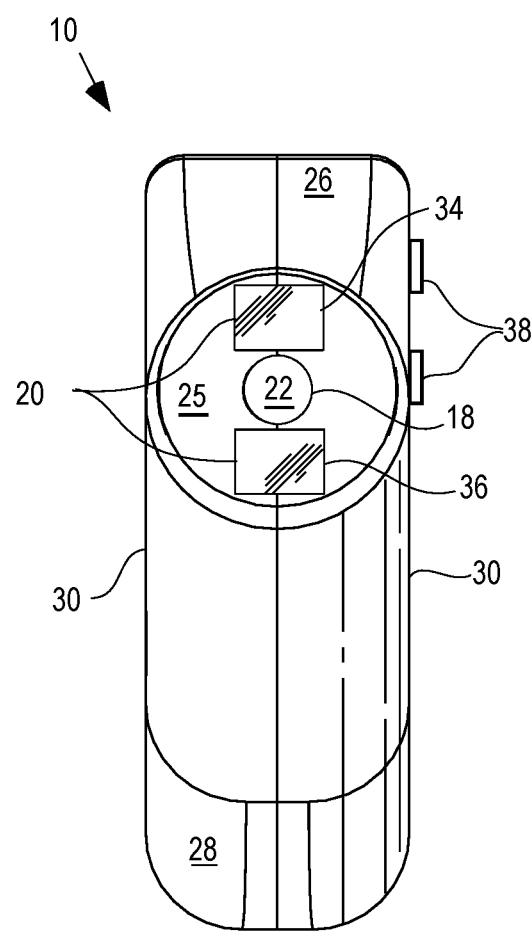
FIG. 3 is a front view of the apparatus of FIG. 1.

With reference to FIGS. 1-3, an apparatus 10 for the detection of fetal acidosis is provided. The apparatus 10 may have an elongated body 12 with a first end portion 14 and a second end portion 16. In some embodiments, the elongated body may be made from a high-density polyethylene, silicone, low-density polyethylene, synthetic polyisoprene, polyurethane, nitrile, thermoplastic elastomers and polymers or another medical grade polyethylene or polymer. In some forms, the elongated body 12 may be rigid, such as having little to no flex, or semi-rigid, such has having some flex. In some embodiments, the first end portion 14 may be curved for insertion in and travel through a patient's vaginal canal. The first end portion 14 may have about 2°, about 5°, about 10°, about 15°, about 20°, about 25°, about 30°, about 35°, about 40° or about 45° curvature relative to the average plane of the second end portion 16. In some embodiments, the second end portion 16 may be ergonomic to a user's hand. The dimensions and weight of the apparatus 10 also allow for portable use.

Still referring to FIGS. 1-3, a pH sensor 18 may be positioned at the first end portion 14. The pH sensor 18 may be configured to detect pH. However, at least one fetal tissue detector 20 may be provided to detect fetal tissue. Such a fetal tissue detector 20 may detect pulse rate, oxygen saturation of blood, temperature, other physiological parameters of a fetus, or a combination thereof. The at least one fetal tissue detector 20 may also be a laparoscope or camera. Although an exposed end 22 of the pH sensor 18 may be visible at the first end portion 14 of the elongated body 12, the remainder of the pH sensor 18 may be housed in an internal cavity 42 of the elongated body 12 and not visible to a user unless the elongated body 12 is opened. In one form, the pH sensor 18 may be substantially flush with an end of the first end portion 14. In other forms, the exposed end 22 of the pH sensor 18 may be extended from the first end portion 14 so as to contact the fetus before any other part of the apparatus 10. For example, the pH sensor 18 may extend about 1 mm, about 2 mm, about 3 mm, about 4 mm, about 5 mm, or other desired distance. In yet other forms, the exposed end 22 of the pH sensor 18 may be recessed from a front 25 of the elongated body 12, such that the front 25 may contact the fetus prior to the pH sensor 18 contacting the fetus. With such an embodiment, the front 25 of the elongated body 12 may be made from material that permits compression thus allowing the exposed end 22 of the pH sensor 18 to contact the fetus. Alternatively, the first end portion 14 of elongated body 12 may also have a mechanism to slightly retreat to allow the exposed end 22 of the pH sensor 18 to contact the fetus.

The pH sensor's 18 output may be shown on a display 24. In some embodiments, the display may be positioned at various locations on the second end portion 16 of the elongated body 12, such as the front 25, top 26, bottom 28, side 30, or rear 32 of the second end portion 16. In addition to displaying an alphanumeric output from the pH sensor 18, the display 24 may also show color to reflect an interpretation of the output. In some embodiments, a first color, such as red, on the display may indicate abnormal range where current fetal acidosis is reflected by a low pH and requires the need for urgent intervention. A low pH may include a pH less than about 6.2, less than about 6.1, less than about 6.0, less than about 5.9, less than about 5.8, or less than a pH determined by a medical professional. A second color, such as yellow, on the display may indicate an elevated range where fetal acidosis is more likely reflected by a moderately low pH and requires the need for conservative measures. A moderately low pH may include a pH between 6.2 and 7.0, between 6.3 and 7.0, between 6.3 and 6.9, between 6.4 and 7.0, between 6.4 and 6.9, between 6.5 and 7.0, between 6.5 and 6.8, or a pH in a range determined by a medical professional. A third color, such as green, on the display may indicate a normal range where the fetus is not suffering or not more likely to suffer fetal acidosis as indicated by a normal pH, which may include a pH greater than about 6.8, greater than about 6.9, greater than about 7.0, or greater than a pH determined by a medical professional. In some forms, an abnormal range indicating fetal acidosis or an elevated range where fetal acidosis is more likely may be further supported by a low oxygen saturation level in the fetus's blood, e.g. a oxygen saturation level of less than about 58%, or a high fetal pulse rate, e.g., a fetal pulse rate over 160 beats per minute. In one form, a diagnosis of fetal acidosis may also depend on the changing trend in pH, oxygen saturation level, or pulse rate of the fetus if multiple measurements are taken.

Still referring to FIGS. 1-3, at least one fetal tissue detector 20 may be located in the first end portion 14 of the elongated body 12. The at least one fetal tissue detector 20 may include a pressure sensor, an optical sensor, an infrared sensor, a pressure switch, a laparoscopic camera, a laparoscopic light, an infrared light, a pulse oximeter, or a combination thereof. In one form, the at least one fetal tissue detector 20 may be located adjacent to the pH sensor 18. In one embodiment, the at least one fetal tissue detector 20 may be a pulse oximeter with an emitter 34 and a photodetector 36. The emitter 34 may include Light Emitting Diodes (LEDs) that emit light of different peak emission wavelengths, including, but not limited to, infrared light. The light may pass through the fetus's skin may be reflected off the fetus's subcutaneous bone and tissue before being received by the photodetector 36. The change in absorbance of the light emitted at each wavelength may be correlated to the level of oxygen saturation in the fetus's blood. The rate of change of the absorbance may be correlated to the observed pulse rate, which may be used to confirm contact with the fetus. For example, if the observed pulse rate is high as compared to the external pulse rate of the patient, then contact with the fetus may be confirmed. For example, during labor, a patient may have a pulse rate of 118 beats per minute, and the observed pulse rate may be 145 beats per minute, which may confirm contact with the fetus.

In other embodiments, a laparoscopic light and/or camera may provide the user a visual indication to the user when the apparatus 10 has contacted a surface of the fetus.

Referring to FIG. 1, the apparatus 10 may also have controls 38 on the second end portion 16 of the elongated body 12 including, but not limited to, power control, calibration control, and mode control. The power control may turn the apparatus 10 on and off. The calibration control may allow the pH sensor 18 to be calibrated against a solution with a known pH, such as deionized water. The mode control may allow a user to set the display 24 to show a particular physiological parameter, such as pH, pulse rate, or oxygen saturation level. The controls 38 may be operatively coupled to a microprocessor as described below. In one form, the controls 38 may be located on a side 30 of the second end portion 16. In another embodiment, the controls 38 may be located on the rear 32 of the second end portion 16 or anywhere else a user can access the controls 38 while the first end portion 14 is inserted into a patient's vaginal canal. In one form, the controls 38 may be located on the display 24. In another form, the controls 38 may be located on a remote display, such as a mobile phone, a computer tablet, a laptop computer, an external monitor, or external medical equipment.

Referring to FIG. 3, the pH sensor 18 and the at least one fetal tissue detector 20 may be adjacent to each other on the first end portion 14. However, other locations are possible.

In one form, the apparatus 10 may have a pH sensor 18 and at least one fetal tissue detector 20 that may be an optical sensor, such as a laparoscopic camera, a laparoscopic light, or a pulse oximeter with an emitter 34 and a photodetector 36. In another form, the apparatus 10 may have a pH sensor 18; an optical sensor, such as a laparoscopic camera, a laparoscopic light, or a pulse oximeter with an emitter 34 and a photodetector 36; and a pressure sensor, as described below. In some forms, the pH sensor 18 or the pulse oximeter may not transmit information, such as a pH reading or a pulse rate reading, respectively, to a microprocessor until the pressure sensor first obtains a pressure reading (i.e., contacts a surface.) The information transmitted to the microprocessor may include, but are not limited to, pH readings, blood oxygen saturation levels, pulse rate reading, temperature, and metabolic rate of tissue. According to one form, the apparatus 10 may a pH sensor 18 and multiple, at least one fetal tissue detectors 20, such as a pressure sensor, a pressure switch, an optical sensor, a laparoscopic camera, a laparoscopic light, a pulse oximeter, or the like, in combination with each other.

Additionally, in some embodiments which may include a pulse oximeter, the pH sensor 18 and the pulse oximeter may alternately transmit information, such as a pH reading and a pulse rate, respectively, to a microprocessor 44, with neither the pH sensor 18 nor the pulse oximeter transmitting information to the microprocessor 44 at the same time. In some embodiments, the pH sensor 18 is a potentiometer, where the difference between a pH electrode and a reference electrode is measured to determine the pH. Therefore, the microprocessor 44 may not accept the information received from the pH sensor 18 as accurate unless the emitter 34 is not transmitting light so as to avoid current from the optical sensor interfering with pH reading from the pH sensor 18.

Figure 4:
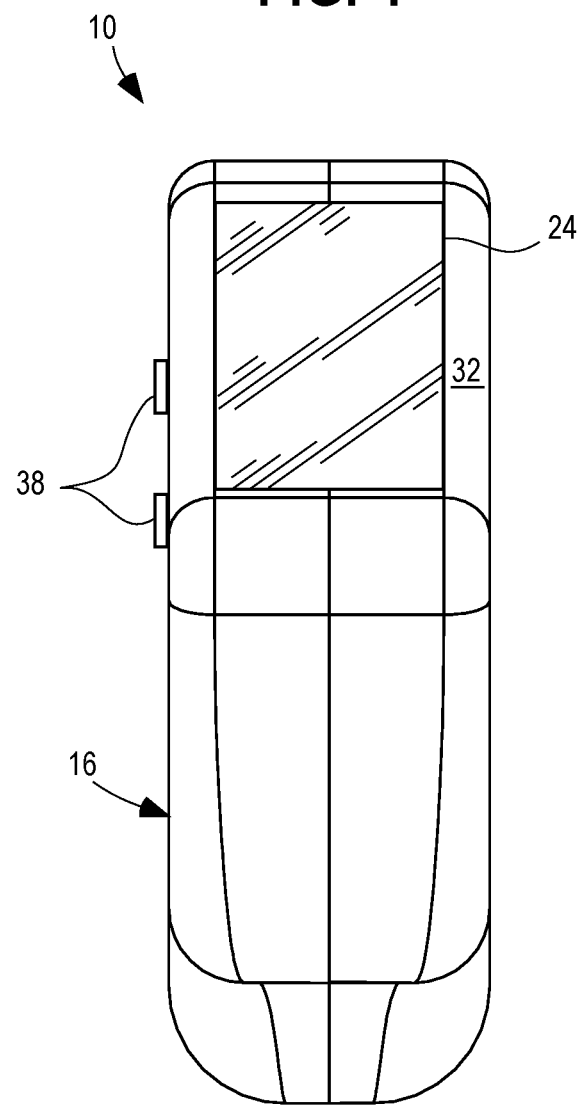
FIG. 4 is a rear view of the apparatus of FIG. 1.

Referring to FIG. 4, the display 24 may be positioned on the rear 32 of the second end portion 16. However, the display 24 may also be located on the top 26 or the side 30 of the second end portion 16, such that the display 24 is visible to the user when the first end portion 14 of the apparatus 10 is inserted into a patient's vaginal canal.

Referring to FIG. 5, the pH sensor 18 may be operatively coupled to a pH meter line 40 in the internal cavity 42 of the elongated body 12. The pH meter line 40 may be in wired communication with the microprocessor 44 such that the microprocessor 44 receives information via the pH meter line 40. In some embodiments, the pH sensor 18 may be in wireless communication with a microprocessor 44. In another form, the display 24 may be remote, such as located on a mobile phone, a computer tablet, a laptop computer, an external monitor, or external medical equipment.

In some embodiments, the pH sensor 18 may be secured to the first end portion 14 of the elongated body 12 via epoxy or another adhesive substance. In such embodiments, the epoxy may act as a moisture barrier for the pH sensor 18, insulate the environment around the pH sensor 18, and improve structural strength near the pH sensor 18. In other embodiments, the pH sensor 18 may be secured to sensor receivers 46, such as ribs, grommets, brackets, suspended and flexible substrates, or a combination thereof, to add support and rigidity to the pH sensor 18. The use of sensor receivers 46 rather than epoxy may reduce the cost and reduce manufacturing and curing time. In some forms, the pH sensor 18 may be soft mounted to the first end portion 14 of the elongated body 12 to permit slight movement of pH sensor 18.

Still referring to FIG. 5, a pressure sensor 48 may also be located in the first end portion 14 of the elongated body 12. In such embodiments, the pressure sensor 48 may alert the user when the apparatus 10 has contacted a surface on the fetus. The pressure sensor 48 may be located adjacent to the pH sensor 18, farther away from second end portion 16 than the pH sensor 18, or between the pH sensor 18 and the second end portion 16 of the apparatus 10. In some embodiments, the pressure sensor 48 may surround a portion of the pH sensor 18. In one form, the pressure sensor 48 may be suspended in flexible, semi-rigid substrate. In one embodiment, the pressure sensor 48 may be sloped-shaped. In another embodiment, the pressure sensor 48 may not be sloped-shaped.

In one embodiment, shown in FIG. 5, the pressure sensor 48 is positioned between the pH sensor 18 and the second end portion 16 of the apparatus 10. The pH sensor 18 is soft mounted to the internal cavity 42 with sensor receivers 46. When the exposed end 22 of the pH sensor 18 contacts a surface, the pH sensor 18 may depress the pressure sensor 48 which may close a circuit within the pressure sensor base 50 (i.e., obtain a pressure reading) to allow the pH sensor 18 to transmit information to the microprocessor 44 via the pH meter line 40. In one form, the pH sensor 18 may wirelessly transmit information to the microprocessor 44.

Still referring to the embodiment in FIG. 5, the at least one fetal tissue detector 20 may be a pulse oximeter with an emitter 34 and a photodetector 36. The emitter 34 may be may be in wired communication with the microprocessor 44 such that the microprocessor 44 transmits information, via the emitter line 52, to direct the emitter 34 to emit light. In some embodiments, the emitter 34 may be in wireless communication with the microprocessor 44. The photodetector 36 may be in wired communications with the microprocessor 44 such that the microprocessor 44 receives information, via the photodetector line 54. In some embodiments, the photodetector 36 may be in wireless communication with the microprocessor 44. In one form, the emitter 34 and photodetector 36 may be in combined in a single device.

In one form, the emitter 34 may be operatively coupled to the pressure sensor base 50, such that light may be emitted from the emitter 34 in response to the pressure sensor 48 being depressed.

The microprocessor 44 may be operatively coupled to a power source 56. In one form, the power source 56 may be a battery. In some embodiments, the battery may be rechargeable. In other embodiments, the battery may be disposable. In some embodiments, the battery may be recharged through a charging port on the apparatus 10 and an external charging station.

In some embodiments, the pH meter line 40 may comprise at least two portions, a proximal portion and a distal portion, with an electrical contact on each portion. The proximal portion of the pH meter line 40 may be disposed closer to the second end portion 16 of the apparatus 10, while the distal portion of the pH meter line 40 may be disposed further from the second end portion 16 and operatively coupled to the pH sensor 18. Such a configuration of the pH meter line 40 may allow for the distal portion with the pH sensor 18 to be removed from the internal cavity 42 and replaced with another distal portion with pH sensor 18. In some embodiments, the second end portion 16 of the elongated body 12 may be uncoupled from the first end portion 14 to allow a user access to the internal cavity 42 to replace the power source 56 or to service the apparatus 10. Additionally, uncoupling the first end portion 14 from the second end portion 16 may allow for the first end portion 14 to be cleaned or sterilized via a medical sterilization device such as an autoclave sterilizer, deionized water, buffer solution, or the like.

In other embodiments, the first end portion 14 may include a coupling mechanism which may support and couple the pH sensor 18 to the pH meter line 40. Such a coupling mechanism may also allow for the pH sensor 18 to be removed from the apparatus 10 and replaced with a different sensor as needed, such as for use on a different patient. With the removable sensors, the elongated body 12 may be reused after sterilization, even though the pH sensor 18 is not reused. In yet other embodiments, the pH sensor 18 is directly coupled to the pH meter line 40 and may not be separated, so the apparatus 10 may not be reused.

In some embodiments, the microprocessor 44 may be operatively coupled to a memory, which may be configured to store the information received from the pH sensor 18 or the at least one fetal tissue sensor 20 for a patient for a certain period of time. In some embodiments, the apparatus 10 may include application circuitry for communication with specific applications or devices such as an external or existing monitoring device's screen which receives information from the microprocessor 44 to alert a user to changes in the pH and temperature of the fetus's blood, heart rate variability of the fetus, or other physiological parameters. The change in pH of the fetus's blood may be indicative of complications in oxygen delivery and may lead to further problems, such as fetal acidosis. The user may receive information regarding the physiological changes from a mobile electronic device that operates an application and receives information from the microprocessor 44.

In one form, the pH sensor 18 and the fetal tissue detector 20 may be operatively coupled to the power source 56 and to the application circuitry such that a microprocessor 44 within the apparatus 10 may not be needed.

With reference to FIG. 6, a protective sheath 58 may be provided to protect the pH sensor 18 from exposure to fluid during insertion in and travel through the vaginal canal of a patient. In some embodiments, the protective sheath 58 may cover a substantial portion of the first end portion 14 of the elongated body 12. In some embodiments, the protective sheath 58 may not obscure the display 24 or the controls 38 from the user. The protective sheath 58 may be made from a material impervious to moisture, for example, natural rubber latex, nitrile, synthetic polyisoprene, or the like. The protective sheath 58 may have an area of weakness 60 near the pH sensor 18. In some embodiments, the area of weakness 60 may be a scored section on the protective sheath 58. In some embodiments, the area of weakness 60 may be created by one or multiple laser scores to the front or back of the material. In other embodiments, the area of weakness 60 may be created by one or more slits or cuts. Such slits or cuts may be made with cutting dies, knives, razors or other apparatus, and may comprise, e.g., a single, long cut or a series of short, jagged cuts in the area of weakness.

In one form, prior to using the apparatus 10, a user may calibrate the pH sensor 18, then may apply the protective sheath 58 to the apparatus 10. In another form, the pH sensor 18 may be calibrated by a manufacturer, so the user may not need to calibrate the pH sensor 18 prior to use but may still apply a protective sheath 58 to the apparatus 10. In yet another form, both calibration of the pH sensor 18 and the application of the protective sheath 58 may completed by the manufacturer prior to use.

After the protective sheath 58 is applied to the apparatus 10, the user may then insert the protective-sheath-covered apparatus into the vaginal canal of a patient. The area of weakness 60 of the protective sheath 58 may be scored in a such a manner to allow insertion into a patient's vaginal canal without disrupting the area of weakness 60. FIGS. 7A and 7B show two variations of the area of weakness 60 for the protection sheath 58, but other variations may be possible. In some embodiments, lubrication does not need to be applied to the protective sheath 58 prior to insertion. In other embodiments, a lubricant, such as a water-based lubricant, may be applied to the protective sheath prior to insertion.

With reference to FIG. 8, after inserting the apparatus 10 into the vaginal canal and locating the fetus, the user may apply enough force to the protective sheath 58 in direction 62 away from the pH sensor 18 to disrupt the area of weakness 60 so that the area of weakness 60 opens and exposes the pH sensor 18 to a surface on the fetus. Once the pH of the surface of the fetus is measured, the user may withdraw the apparatus 10 from vaginal canal of the patient. The user may hold the protective sheath 58 during removal of the apparatus 10 from the vaginal canal as to ensure no foreign object debris remains the in the patient.

After the apparatus 10 is removed from the vaginal canal, the user may also completely remove the protective sheath 58 from the apparatus 10. The user may disinfect the pH sensor 18 and/or the fetal tissue detector 20 in response to expecting to use the pH sensor 18 and/or the fetal tissue detector 20 on the same patient. The user may apply a new protective sheath 58 to cover the apparatus 10 for another use on the same patient.

Figure 9:
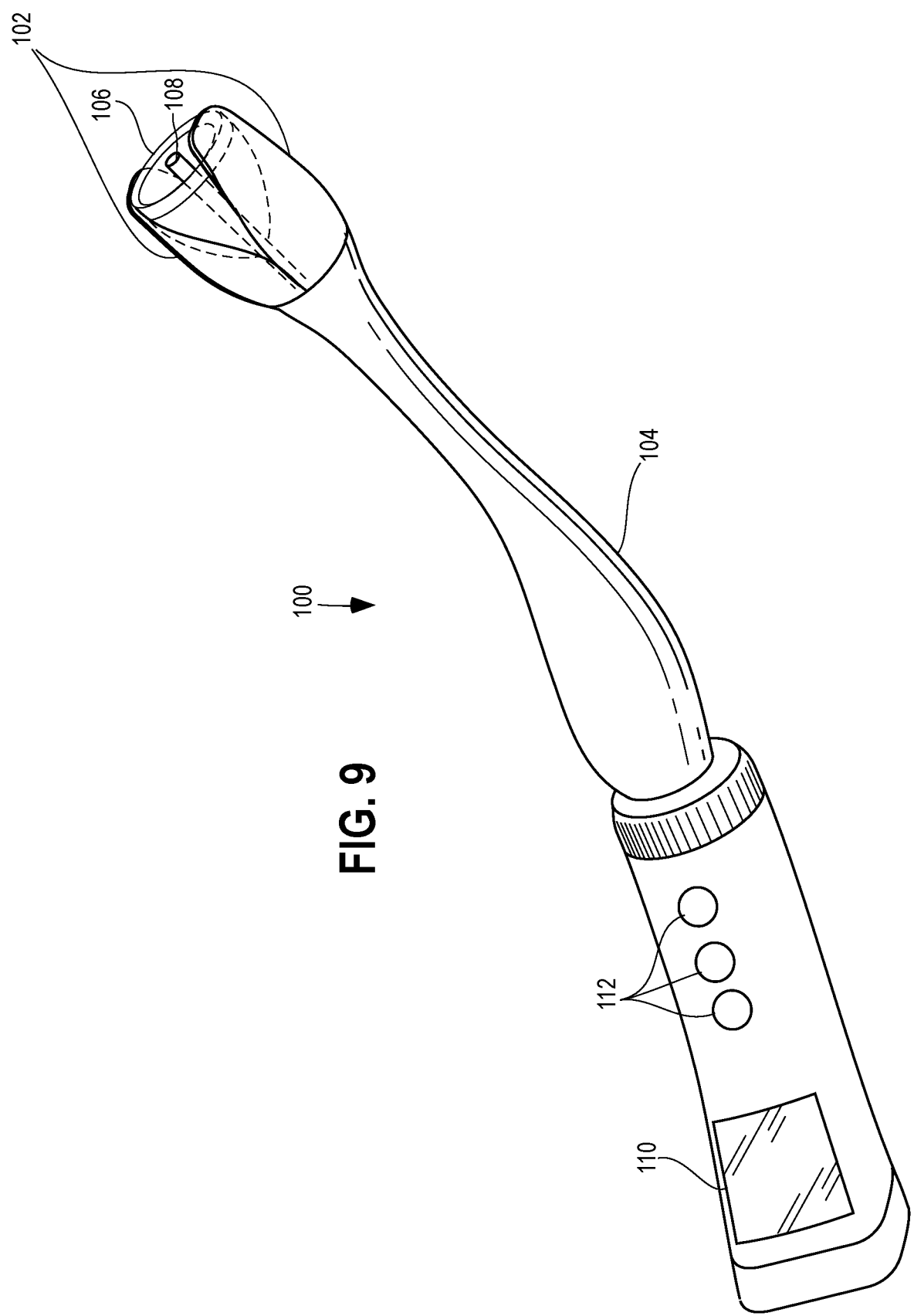
FIG. 9 is a perspective view of another form of a fetal acidosis detection apparatus.

Referring to FIG. 9, a second embodiment of the fetal acidosis detection apparatus 100 is shown and may include similar features, as described above, to the first embodiment except as described below. The apparatus 100 may have a plurality of flaps 102 pivotably coupled to the first end portion 104. In some embodiments, the number of flaps 102 may be at least one, two, three, four, five, or six. The internal cavity may further comprise a mechanism which closes and opens the flaps 102 around an annular receptacle 106 which substantially surrounds the pH sensor 108.

In one form, the pH sensor 108 may be protected by a shield which may be retracted to expose the pH sensor to the skin of the fetus.

Figure 10:
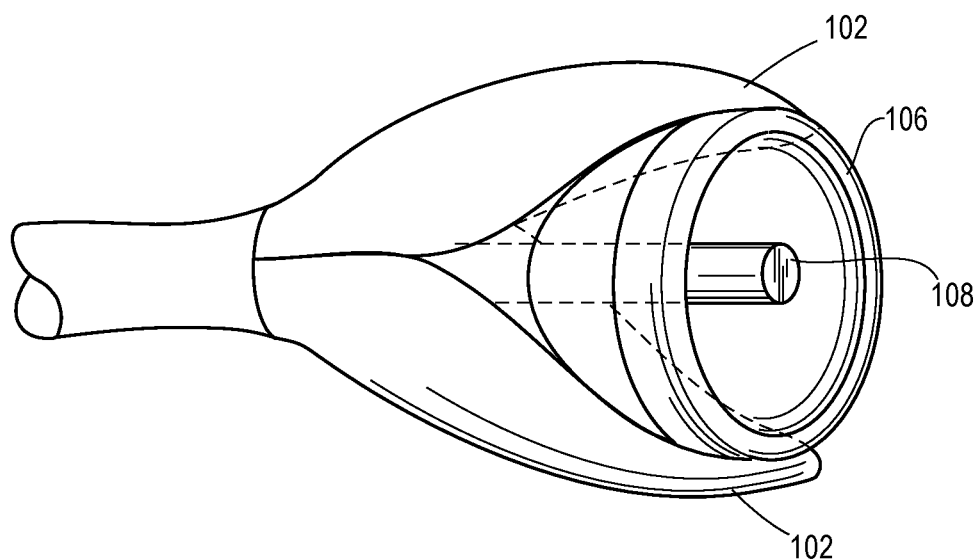
FIG. 10 is an enlarged view of a first end portion of the apparatus of FIG. 9 with a set of flaps open in a first position.

Referring to FIG. 10, in a first position, when the mechanism is not actuated, the flaps 102 are open, and the annular receptacle 106 and the pH sensor 108 are uncovered. For the pH sensor 108 to contact the fetus's skin, the flaps are in the first position.

Figure 11:
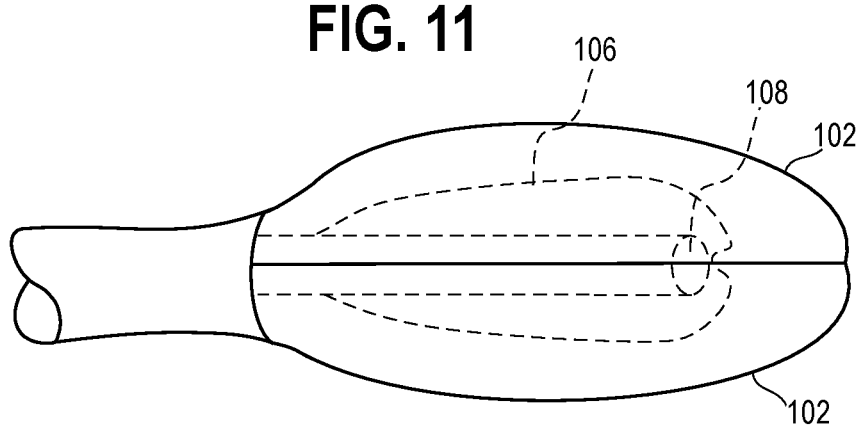
FIG. 11 is an enlarged view of a first end portion of the apparatus of FIG. 9 with a set of flaps closed in a second position.

Referring to FIG. 11, in a second position when the mechanism is actuated by a user, the flaps 102 are closed, and the annular receptacle 106 and the pH sensor 108 are covered by the flaps 102. When the apparatus is inserted into or withdrawn from the vaginal canal, the flaps are in the second position.

However, in another form, the first position of the flaps 102 (i.e., when the mechanism is not actuated) may be the biased to the flaps 102 being closed. In that form, the second position (i.e., when the mechanism is actuated) may open the flaps 102 to expose the pH sensor 108.

In one method of use, a user may actuate a power control to turn on the apparatus 100. After the display 110 indicates that the apparatus 100 is ready by displaying a symbol or a color on the screen or by vibrating, the user may optionally calibrate the apparatus by contacting the pH sensor 108 to a standard solution with a known pH. If the pH reading on the display 110 is the same as the known pH of the standard solution, then the user may press a calibration control 112 to calibrate the apparatus 100. If the pH reading on the display 110 is different, the user may adjust the display measurement to match the pH of the standard solution then press the calibration button.

The user may actuate or not actuate the mechanism, depending on the bias, to close the flaps 102 around the annular receptacle 106 and the pH sensor 108. The user then may insert the apparatus 100 into the vaginal canal until the apparatus 100 nears the fetus. The user may actuate or deactivate the mechanism, depending on the bias, to open the flaps 102 and expose the annular receptacle 106 and the pH sensor. The user may contact the annular receptacle 106 and the pH sensor 108 to the skin of the fetus. The pH of the fetus's skin may be measured and transmitted to the microprocessor 44 for comparison to an internal correlation table programmed in the microprocessor 44. The measurement may be stored in the memory of the microprocessor 44 and shown on the display 110. In one form, the microprocessor 44 may also have programming to adjust the information received from the pH sensor 18 based on the skin tone of the fetus's parents.

If the pH reading is in the normal range, the user may remove the apparatus 100 for use again at a later time. To remove the apparatus 100, the user may move the pH sensor 108 and annular receptacle 106 away from the fetus's skin, then may actuate the mechanism, which closes the flaps 102 into the second position over the annular receptacle 106 and the pH sensor 108. The apparatus may then be withdrawn from the vaginal canal. The apparatus 100 may be put aside in a sterile area for use again on the same patient at a later time in the delivery. If the pH reading is in the abnormal range, then the user would still remove the apparatus 100 but would also begin steps for intervention, such as urgent delivery.

The fetal acidosis detection apparatus 10, 100 may be provided as part of a set with additional items for use with the apparatus 10, 100. For example, a tray may be included to hold the apparatus 10, 100 when not in use on a patient. Further, disinfecting cloths may be included to clean the apparatus 10, 100 between uses on the same patient. To calibrate the apparatus prior to use, a buffering solution of deionized water may be included to help ensure accurate measurements of the pH sensor 18, 108. Bags or other containers may also be included with the apparatus 10, 100 for disposal of the sensor after use on a patient.

Those skilled in the art will recognize that a wide variety of modifications, alterations, and combinations may be made with respect to the above described embodiments without departing from the scope of the invention, and that such modifications, alterations, and combinations are to be viewed as being within the ambit of the inventive concept.

What is claimed is:

1. An apparatus for detecting fetal acidosis comprising:
    an elongated body with a first end portion and a second end portion; the first end portion including a pH sensor with an exposed end, the pH sensor comprising a potentiometer, and a fetal tissue detector comprising an optical sensor, the optical sensor comprising an emitter and a photodetector; and the second end portion configured for grasping by a user; and
    a microprocessor operatively coupled to the pH sensor and to the fetal tissue detector;
    wherein the pH sensor is operative to transmit data to the microprocessor during a first time period;
    wherein the fetal tissue detector is operative to transmit data to the microprocessor during a second time period;
    wherein the first time period is different from the second time period;
    wherein the microprocessor is configured to determine whether the emitter is transmitting light and to reject data received from the pH sensor unless the emitter is not transmitting light.

2. The apparatus of claim 1, wherein the optical sensor is a pulse oximeter that determines pulse rate readings.

3. The apparatus of claim 1, wherein the fetal tissue detector is located between the exposed end of the pH sensor and the second end portion of the elongated body.

4. The apparatus of claim 1, wherein the pH sensor determines a pH reading in response to the fetal tissue detector confirming contact with a fetus.

5. The apparatus of claim 1, wherein the elongated body comprises silicone, high density polyethylene, low density polyethylene, or a combination thereof.

6. The apparatus of claim 1, wherein the elongated body is curved for insertion into a vaginal canal of a patient.

7. The apparatus of claim 1, further comprising a protective sheath surrounding the first end portion.

8. The apparatus of claim 7, wherein the protective sheath includes an area of weakness.

9. The apparatus of claim 8, wherein when the area of weakness is disrupted, the pH sensor is exposed.

10. The apparatus of claim 1, wherein the pH sensor is removably secured to the first end portion.

11. The apparatus of claim 1, further comprising a memory operatively coupled to the pH sensor to store a pH reading.

12. The apparatus of claim 1, further comprising a display operatively coupled to the pH sensor.

13. The apparatus of claim 12, wherein the display includes status indicators indicating whether the pH reading is in a normal, elevated, or abnormal range for fetal acidosis.

14. A method for detecting fetal acidosis using the apparatus of claim 1, wherein the method includes:
    inserting the first end portion into a patient's vaginal canal;
    determining that the pH sensor is contacting a fetus via the fetal tissue detector;
    maintaining contact of the pH sensor with the fetus; and
    determining pH readings from the pH sensor's contact with the fetus via the microprocessor;
    wherein determining the pH readings from the pH sensor's contact with the fetus via the microprocessor further comprises:
        determining for at least one pH reading that the emitter is transmitting light and rejecting the pH reading.

15. The method of claim 14, wherein determining the pH readings from the pH sensor's contact with the fetus does not include removing tissue or blood from the fetus.

16. The method of claim 14, wherein determining that the pH sensor is contacting the fetus via the fetal tissue detector is achieved by comparing a pulse rate reading from the optical sensor with an external pulse rate reading from the patient.

17. The method of claim 14, further comprising storing the pH reading in a memory operatively coupled to the pH sensor.

18. The method of claim 17 further comprising disrupting an area of weakness on a protective sheath surrounding the first end portion to expose the pH sensor to the fetus.

* * * * *